United States Patent
Jiang et al.

(10) Patent No.: US 9,256,934 B2
(45) Date of Patent: Feb. 9, 2016

(54) ENHANCED IMAGE RECONSTRUCTION IN PHOTOACOUSTIC TOMOGRAPHY

(75) Inventors: Huabei Jiang, Gainesville, FL (US); Lei Yao, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 60 days.

(21) Appl. No.: 14/009,584

(22) PCT Filed: Apr. 6, 2012

(86) PCT No.: PCT/US2012/032473
§ 371 (c)(1),
(2), (4) Date: Oct. 3, 2013

(87) PCT Pub. No.: WO2012/138965
PCT Pub. Date: Oct. 11, 2012

(65) Prior Publication Data
US 2014/0029829 A1    Jan. 30, 2014

Related U.S. Application Data

(60) Provisional application No. 61/473,348, filed on Apr. 8, 2011.

(51) Int. Cl.
*G06K 9/00*    (2006.01)
*G06T 7/00*    (2006.01)
*A61B 8/13*    (2006.01)
*A61B 8/08*    (2006.01)
*A61B 5/00*    (2006.01)

(52) U.S. Cl.
CPC .............. *G06T 7/0012* (2013.01); *A61B 5/0095* (2013.01); *A61B 5/72* (2013.01); *A61B 8/13* (2013.01); *A61B 8/5207* (2013.01)

(58) Field of Classification Search
CPC .......... A61B 5/0095; A61B 8/13; A61B 5/72; A61B 8/5207; A61B 6/032; A61B 6/508; A61B 5/7232; A61B 6/4007; A61B 5/055; A61B 5/489; A61B 6/037; A61B 6/4417; A61B 6/482; A61B 6/484; A61B 6/507; A61B 6/5205; A61B 6/5235; G06T 7/0012; G06T 11/006
See application file for complete search history.

(56) References Cited

U.S. PATENT DOCUMENTS

2008/0107319 A1    5/2008    Chang et al.
2008/0267484 A1    10/2008    Chen
(Continued)

OTHER PUBLICATIONS

The International Preliminary Report on Patentability dated Oct. 17, 2013.
(Continued)

*Primary Examiner* — Tom Y Lu
(74) *Attorney, Agent, or Firm* — Thomas|Horstemeyer, LLP.

(57) ABSTRACT

Various embodiments of methods and systems are provided for image reconstruction in photoacoustic tomography. In one embodiment, among others, a method includes obtaining photoacoustic time-domain data; reconstructing an image from the photoacoustic time-domain data using total-variation minimization based photoacoustic tomography reconstruction; and providing the reconstructed image for rendering on a display device. In another embodiment, a system includes a computing device and an image reconstruction program executable in the computing device. The image reconstruction program includes logic that obtains photoacoustic time-domain data; logic that reconstructs an image from the photoacoustic time-domain data using total-variation minimization based photoacoustic tomography reconstruction; and logic that provides the reconstructed image for rendering on a display device.

20 Claims, 17 Drawing Sheets

(56) References Cited

U.S. PATENT DOCUMENTS

| | | |
|---|---|---|
| 2009/0054763 A1 | 2/2009 | Wang et al. |
| 2010/0208965 A1 | 8/2010 | Jiang et al. |
| 2011/0282181 A1* | 11/2011 | Wang et al. ............... 600/407 |

OTHER PUBLICATIONS

The International Search Report and Written Opinion dated Dec. 21, 2012.

* cited by examiner (a)

(a)  (b)

(c)

(d)

(a)

(b)

ENHANCED IMAGE RECONSTRUCTION IN PHOTOACOUSTIC TOMOGRAPHY

CROSS REFERENCE TO RELATED APPLICATIONS

This application is the 35 U.S.C. §371 national stage of PCT application PCT/US2012/32473, filed Apr. 6, 2012, which claims priority to and the benefit of U.S. Provisional Application Ser. No. 61/473,348, filed Apr. 8, 2011, both of which are hereby incorporated by reference herein in their entirety.

BACKGROUND

Biomedical photoacoustic tomography (PAT) is an imaging method for visualizing the internal structure of soft tissues with excellent spatial resolution and satisfactory imaging depth. Conventional PAT can image tissues with high spatial resolution; however a large number of measurements are needed for reconstruction of an image. Extending the required scanning time and number of sensors placed near or on the boundary of an object to pick up the signals. In addition, photoacoustic signals recorded over an aperture that does not enclose the object can result in a limited-view topographic reconstruction. In such cases, the existing reconstruction algorithms often give distorted images with severe artifacts.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1A:
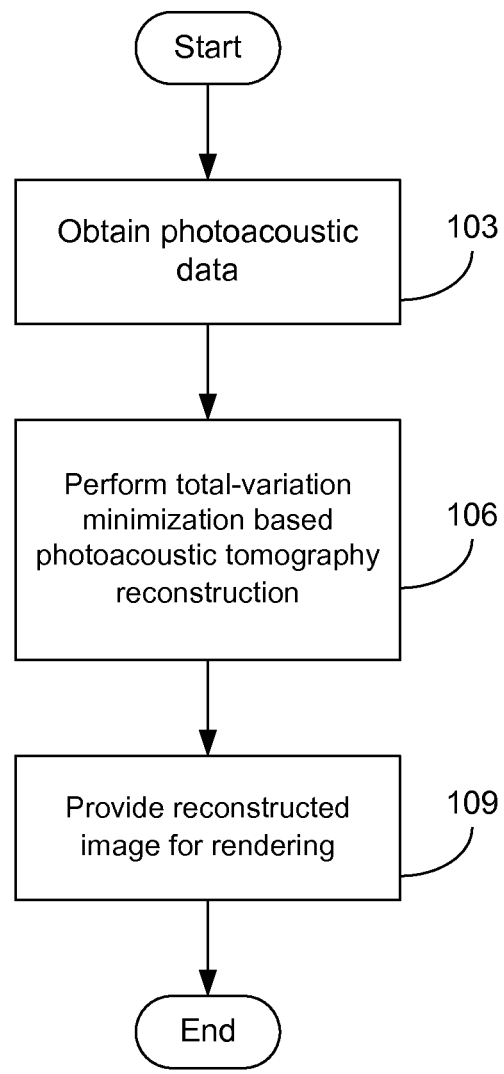
FIGS. 1A and 1B are flow charts illustrating an example of image reconstruction using total-variation minimization based photoacoustic tomography in accordance with various embodiments of the present disclosure.

Disclosed herein are various embodiments of methods and systems related to image reconstruction in photoacoustic tomography. Reference will now be made in detail to the description of the embodiments as illustrated in the drawings, wherein like reference numbers indicate like parts throughout the several views.

Photoacoustic tomography (PAT) is a noninvasive imaging technique that combines the merits of high optical contrast and high ultrasound resolution in a single modality. PAT reconstructs an internal photoacoustic source distribution from measurements acquired by scanning ultrasound detectors over the surface of an excited volume. In a photoacoustic (PA) imaging system such as, e.g., the system described in U.S. patent application entitled "Method and Apparatus for Tomographic Imaging of Absolute Optical Absorption Coefficient in Turbid Media Using Combined Photoacoustic and Diffusing Light Measurements," having Ser. No. 12/668,976, filed Jan. 13, 2010, the entirety of which is hereby incorporated by reference, pulsed light from a laser is coupled into the volume via an optical subsystem and acoustic signals are generated. The generated PA signals (ultrasonic waves) are detected by ultrasonic transducers to form images. Temporal and spatial PA measurements provide the information for image reconstruction.

In PAT, the Helmholtz-like photoacoustic (PA) wave equation may be used as an accurate model for describing laser-induced acoustic wave propagation in tissue. While analytical reconstruction methods have been used for PA image reconstructions, the finite element method (FEM)-based approach appears to be particularly powerful in this regard. The advantages of the FEM-based PAT method include (1) quantitative imaging capability by recovering optical absorption coefficient, (2) elimination of the assumption of homogeneous acoustic medium needed in analytical methods, (3) accommodation of object boundary irregularity, and (4) appropriate boundary conditions implementations.

The disclosed finite element PAT approaches are based on a regularized iterative Newton method, which have been tested and evaluated using extensive simulations and phantom experiments in both the frequency and time domain. Compared with the frequency domain method, the time domain method can reconstruct images with less background artifacts, especially when the target size is very small, and can provide a more accurately recovered target size. However, measurement noises still affect the quantitative accuracy of the reconstructed images. For example, errors for quantitatively recovering optical absorption coefficient can be as large as 10% for simulated data with 5% noise added and 20% for experimental data.

To reduce the noise effect and further enhance the quantitative accuracy of PA image reconstruction, a total variation minimization (TVM) scheme within a FEM-based reconstruction framework can be utilized. The reconstruction algorithms are based on a least squares criteria (e.g., the regularized Newton method) that stand on the statistical argument that the least-squares estimation is the best estimator over an entire ensemble of all possible pictures. Total variation, on the other hand, measures the oscillations of a given function and does not unduly punish discontinuities. Hence, a hybrid of these two minimization schemes may provide higher-quality image reconstructions. Described herein is an unconstrained TVM FEM-based iterative reconstruction algorithm that offers excellent PA image reconstruction from few-detector and limited-angle data. This can greatly reduce the required scanning time and the number of ultrasound sensors placed near or on the boundary of the object excited by the laser-induced acoustic signals.

To describe the TVM method, the FEM-based regularized Newton method in the time domain is first discussed. The time domain PA wave equation in tissue can be described as follows:

$$\nabla^2 p(r,t) - \frac{1}{v_0^2}\frac{\partial^2 p(r,t)}{\partial t^2} = -\frac{\Phi(r)\beta}{C_p}\frac{\partial J(t)}{\partial t}, \quad \text{EQN. (1)}$$

where p is the pressure wave, $v_0$ is the speed of acoustic wave in the medium, $\beta$ is the thermal expansion coefficient, $C_p$ is the specific heat, $\Phi$ is the absorbed energy density, and $J(t) = \delta(t-t_0)$ is assumed.

Expanding p as the sum of coefficients multiplied by a set of basis function $\psi_j$, $p=\Sigma p_j \psi_j$, the finite element discretization of EQN. (1) can then be written as:

$$\sum_{j=1}^{N} p_j\left[\int_S \nabla\psi_i \cdot \nabla\psi_j \, dS\right] + \sum_{j=1}^{N} \ddot{p}_j\left[\int_S \frac{1}{v_0^2}\psi_i\psi_j \, dS\right] - \quad \text{EQN. (2)}$$

$$\oint_l \psi_i \nabla p \cdot \hat{n} \, dl = \int_S \frac{\beta\Phi}{C_p}\frac{\partial J}{\partial t}\psi_i \, dS.$$

Where the first-order absorbing boundary conditions are:

$$\nabla p \cdot \hat{n} = -\frac{1}{v_0}\frac{\partial p}{\partial t} - \frac{p}{2r}. \quad \text{EQN. (3)}$$

where $\hat{n}$ is the unit normal vector.

In both the forward and inverse calculations, the unknown coefficient $\Phi$ needs to be expanded in a similar fashion top as a sum of unknown parameters multiplied by a set of locally spatially varying Lagrange polynomial basis functions. Thus, the matrix form of EQN. (2) becomes $$|K|\{p\}+|C|\{\dot{p}\}+|M|\{\ddot{p}\}=\{B\}. \quad \text{EQN. (4)}$$

where the elements of matrix [K], [C], and [M] are given by:

$$K_{ij} = \int_S \nabla\psi_i \cdot \nabla\psi_j \, dS + \frac{1}{2r}\oint_l \psi_i\psi_j \, dl; \quad \text{EQN. (5)}$$

-continued $$C_{ij} = \frac{1}{v_0}\oint_l \psi_i\psi_j \, dl;$$

$$M_{ij} = \frac{1}{v_0^2}\int_S \psi_i\psi_j \, dS;$$

and the column vectors $\{B\}$, $\{p\}$, $\{\dot{p}\}$, and $\{\ddot{p}\}$ are:

$$B_i = \frac{\beta}{C_P}\int_S \psi_i\left(\sum_k \psi_k\Phi_k\right)dS \cdot \frac{\partial J}{\partial t}; \quad \text{EQN. (6)}$$

$$\{p\} = \{p_1 \cdot p_2 \cdots p_N\}^T;$$
$$\{\dot{p}\} = \{\dot{p}_1 \cdot \dot{p}_2 \cdots \dot{p}_N\}^T;$$
$$\{\ddot{p}\} = \{\ddot{p}_1 \cdot \ddot{p}_2 \cdots \ddot{p}_N\}^T;$$

Here, the Newmark's time-stepping scheme is used for the discretization of time dimension, which is an implicit method for second-order propagation equations such as EQN. (4).

To form an image from a presumably uniform initial guess of the absorbed energy density distribution, a method of updating $\Phi$ from its starting value is used. The update can be accomplished through least-squares minimization of the following functional:

$$F(p,\Phi) = \sum_{j=1}^{M}(P_j^o - p_j^c)^2. \quad \text{EQN. (7)}$$

where $p_j^o$ and $p_j^c$ are observed and computed acoustic field data for j=1, 2, . . . M boundary locations. Using the regularized Newton method, the following equation for updating $\Phi$ is obtained:

$$(\Im^T\Im+\lambda I)\Delta\chi=\Im^T(p^o-p^c). \quad \text{EQN. (8)}$$

where $p^o=(p_1^o, p_2^o, \ldots p_M^o)^T$, $p^c=(p_1^c, p_2^c \ldots p_M^c)^T$, $\Delta\chi$ is the update vector for the absorbed optical energy density, $\Im$ is the Jacobian matrix formed by $\partial p/\partial\Phi$ at the boundary measurement sites, $\lambda$ is the regularization parameter determined by combined Marquardt and Tikhonov regularization schemes, and I is the identity matrix.

Two approaches may be used for minimizing total variation: a constrained minimization through the solution of the nonlinear PA equation and an unconstrained minimization by addition of the total variation as a penalty term to the least-squares functional. From a computational standpoint, unconstrained minimizations are much easier to implement and require fewer modifications to the existing algorithm. Thus, an unconstrained TVM is used.

The total variation of $\Phi$ is incorporated as a penalty term by defining a new functional:

$$\tilde{F}(p,\Phi)=F(p,\Phi)+L(\Phi). \quad \text{EQN. (9)}$$

Here, $$L(\Phi)=\int\sqrt{\omega_\Phi^2|\nabla\Phi|^2+\delta^2}\,dxdy \quad \text{EQN. (10)}$$

is the penalty term, and $\omega_\Phi$ and $\delta$ are typically positive parameters that need to be determined numerically. The minimization of EQN. (9) proceeds by the differentiation of $\tilde{F}$ with respect to each nodal parameter that constitutes the $\Phi$ distribution; simultaneously, all these relations are set to zero. These steps lead to the following nonlinear system of equations $$\frac{\partial \hat{F}}{\partial \Phi_i} = -\sum_{j=1}^{M}(p_j^o - p_j^c)\frac{\partial p_j^c}{\partial \Phi_i} + V_i \cdot (i = 1 \cdot 2 \ldots N). \quad \text{EQN. (11)}$$

where $$V_i = \frac{\partial L}{\partial \Phi_i} = \quad \text{EQN. (12)}$$

$$\int \frac{\omega_\Phi^2 \left[\left(\sum_{k=1}^{N}\Phi_k\frac{\partial \psi_k}{\partial x}\right)\frac{\partial \psi_i}{\partial x} + \left(\sum_{k=1}^{N}\Phi_k\frac{\partial \psi_k}{\partial x}\right)\frac{\partial \psi_i}{\partial x}\right]}{\sqrt{\omega_\Phi^2 \left[\left(\sum_{k=1}^{N}\Phi_k\frac{\partial \psi_k}{\partial x}\right)^2 + \left(\sum_{k=1}^{N}\Phi_k\frac{\partial \psi_k}{\partial x}\right)^2\right] + \delta^2}} dxdy.$$

Similar to EQN. (8), the following matrix equation for a TVM constrained inversion can be obtained:

$$(\Im^T\Im + R + \lambda I)\Delta\chi = \Im^T(p^o - p^c) - V. \quad \text{EQN. (13)}$$

where R is formed by $\partial V/\partial \Phi$:

$$R = \begin{bmatrix} \frac{\partial V_1}{\partial \Phi_1} & \frac{\partial V_1}{\partial \Phi_2} & \cdots & \frac{\partial V_1}{\partial \Phi_N} \\ \frac{\partial V_2}{\partial \Phi_1} & \frac{\partial V_2}{\partial \Phi_2} & \cdots & \frac{\partial V_2}{\partial \Phi_N} \\ \vdots & & \ddots & \vdots \\ \frac{\partial V_N}{\partial \Phi_1} & \frac{\partial V_N}{\partial \Phi_2} & \cdots & \frac{\partial V_N}{\partial \Phi_N} \end{bmatrix} \quad \text{EQN. (14)}$$

and $$V = \{V_1 \cdot V_2 \cdot \ldots V_N\}^T. \quad \text{EQN. (15)}$$

The solution procedure for solving EON. (13) and the regularization parameter selection are identical to those described previously. The solution is iteratively determined until one or more predefined criteria are met. For example, a predefined number of solution iterations may be performed or the solution converges below a predefined threshold.

Figure 1B:
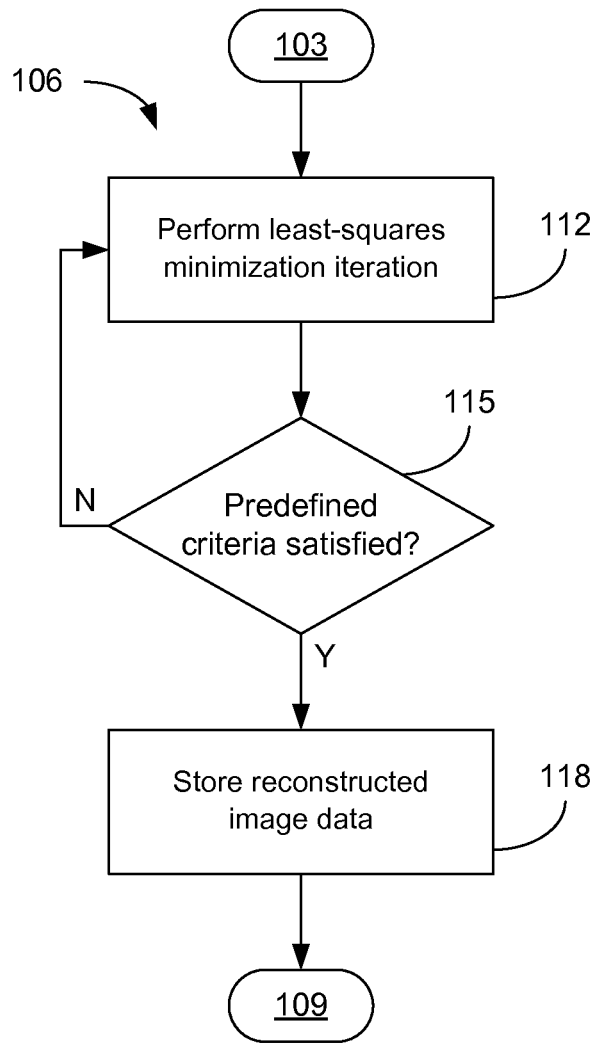

Referring to FIGS. 1A and 1B, shown are flow charts illustrating an example of image reconstruction using total-variation minimization based photoacoustic tomography in accordance with various embodiments of the present disclosure. Beginning with block 103, photoacoustic (PA) time-domain data is obtained. The PA data may be store in memory, from which it may be obtained, or may be obtained from a PA imaging device including a plurality of detectors (or sensors) and a pulsed light source. In some implementations, the PA imaging device may store the PA data in the memory for later access.

In box 106, a total-variation minimization based photoacoustic tomography reconstruction is performed using the PA time-domain data to reconstruct an image. The total-variation minimization based photoacoustic tomography reconstruction is based at least in part upon the functional of EQN. (9), which includes a penalty term based upon variation of absorbed energy density ($\Phi$) such as, e.g., the penalty term given by EQN. (10). EQN. (9) is also based upon observed acoustic field data and computed acoustic field data. In block 109, the absorbed energy density image recovered using the reconstruction method is provided for rendering on a display device.

FIG. 1B shows a flow chart of an example of the total-variation minimization based photoacoustic tomography reconstruction 106 of FIG. 1A. In the example of FIG. 1B, the PA data from box 103 is used to perform a least-squares minimization iteration in box 112. The interation may include a dual-meshing scheme with forward calculation of a first mesh and inverse calculation of a second mesh. The first mesh may be a fine mesh and the second mesh may be a course mesh with fewer nodes and elements than the fine mesh. In block 115, it is determined if the predefined iteration criteria is satisfied. For example, the photoacoustic tomography reconstruction may be performed for a predefined number of iterations or may be complete when the least-squares minimization satisfies a predefined threshold. If it is not satisfied in block 115, the flow returns to block 112 to perform another iteration. If the condition is satisfied, then the calculated results can be stored in block 118 and are provided to box 109 of FIG. 1A for rendering.

The TVM-enhanced reconstruction algorithm was tested and evaluated using both simulated and experimental data. For comparative purposes, reconstructions without the TVM enhancement are also presented. An experimental setup used for collecting phantom data was a pulsed ND: YAG laser based single transducer (1 MHz) scanning system. Three phantom experiments were conducted. In the first two experiments, one or two objects with a size ranging from 3 to 0.5 mm were embedded in a 50 mm-diameter solid cylindrical phantom. The absorption coefficient of the background phantom was 0.01 mm$^{-1}$, while the absorption coefficient of the target(s) was 0.03 mm$^{-1}$. In the last experiment, a single-target-containing phantom was used, aiming to test the capability of detecting a target having a low optical contrast relative to the background phantom. In the last case, the target had an absorption coefficient of 0.015 mm$^{-1}$. The reduced scattering coefficients of the background phantom and targets were 1.0 and 3.0 mm$^{-1}$ for the first two experiments, and 1.0 and 2.0 mm-1 for the last experiment.

In the reconstructions, a dual-meshing scheme was used where the fine mesh used for the forward calculation consisted of 5977 nodes and 11712 elements, while the coarse mesh used for the inverse calculation had 1525 nodes and 2928 elements. All the images obtained from the method without the TVM are the results of three iterations, while those obtained from the TVM-enhanced method are the results of twenty or more iterations. Parallel code was used to speed up these calculations on Beowulf clusters with 8 CPUs. The computational speed may be further increased if clusters with more than 8 CPUs are used. As mentioned above, the parameters $\omega_\Phi$ and $\delta$ were determined through numerical experimentation. From experience, a constant value of $\delta=0.001$ was sufficient for the current experimental studies, while the value of $\omega_\Phi$ is related to the signal-to-noise ratio of the measurements. For these experimental cases, $\omega_\Phi=1.0$ and $\delta=0.001$ was used for the first case, and $\omega_\Phi=0.5$ and $\delta=0.001$ were used for the second and third cases.

Figure 2:
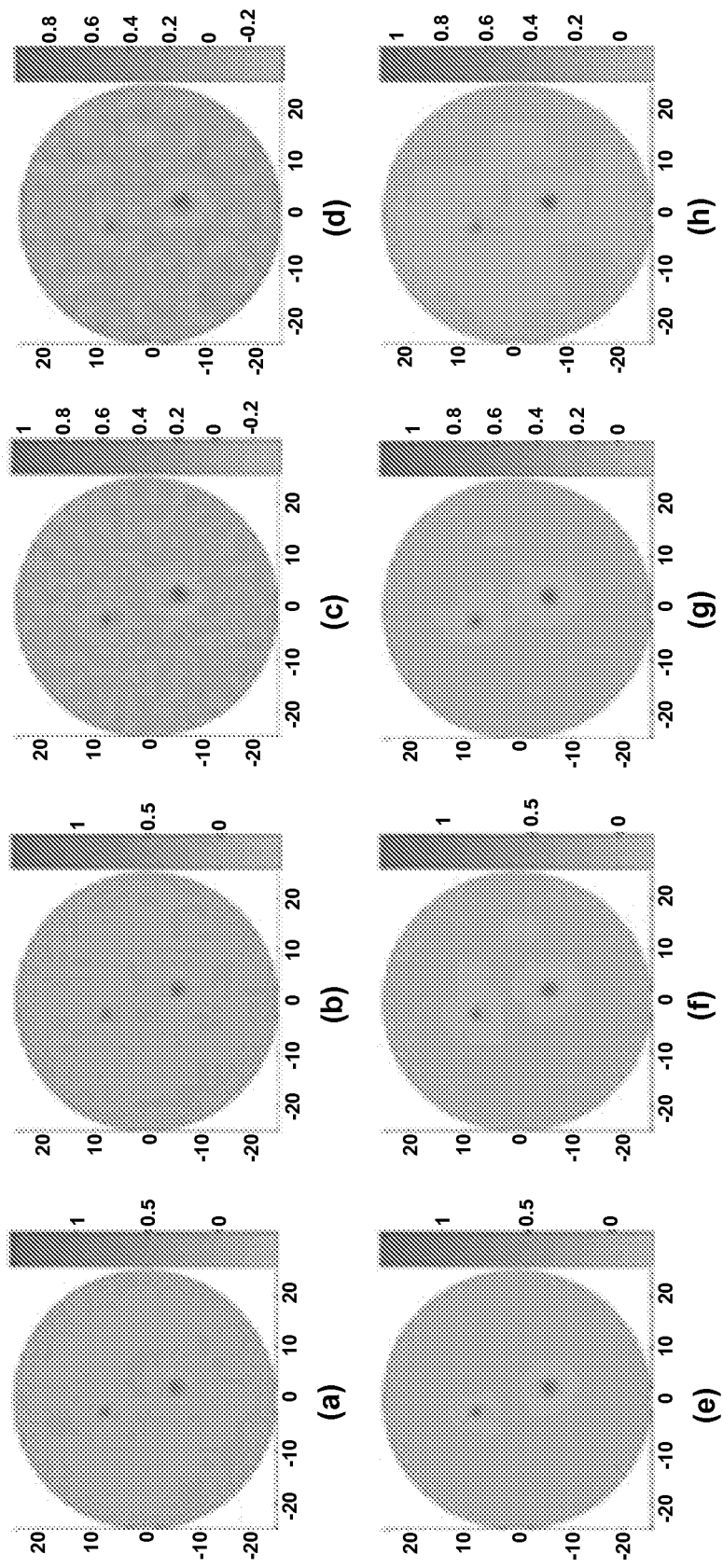
FIGS. 2-5 are examples of photoacoustic images reconstructed using total-variation minimization based photoacoustic tomography of FIGS. 1A and 1B in accordance with various embodiments of the present disclosure.
Figure 3:
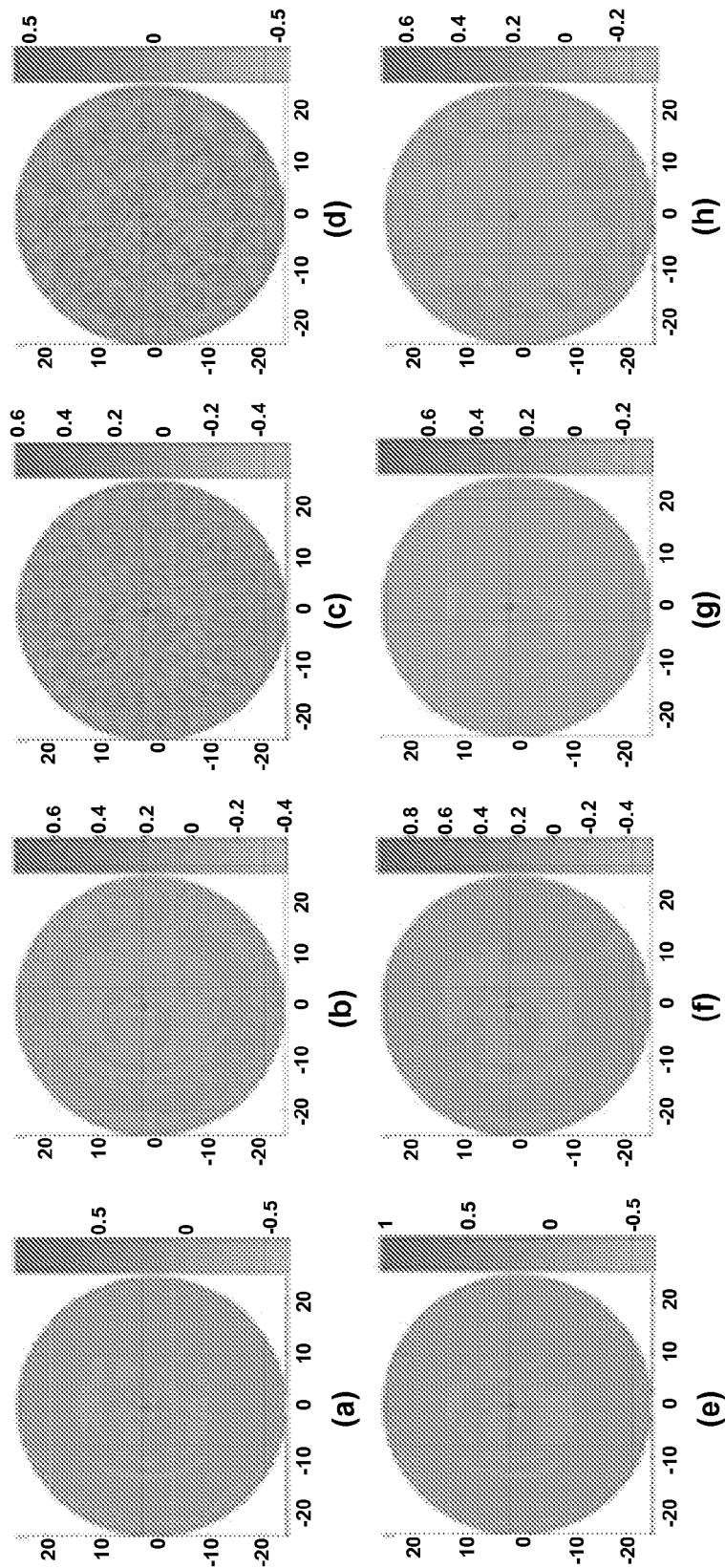
Figure 4:
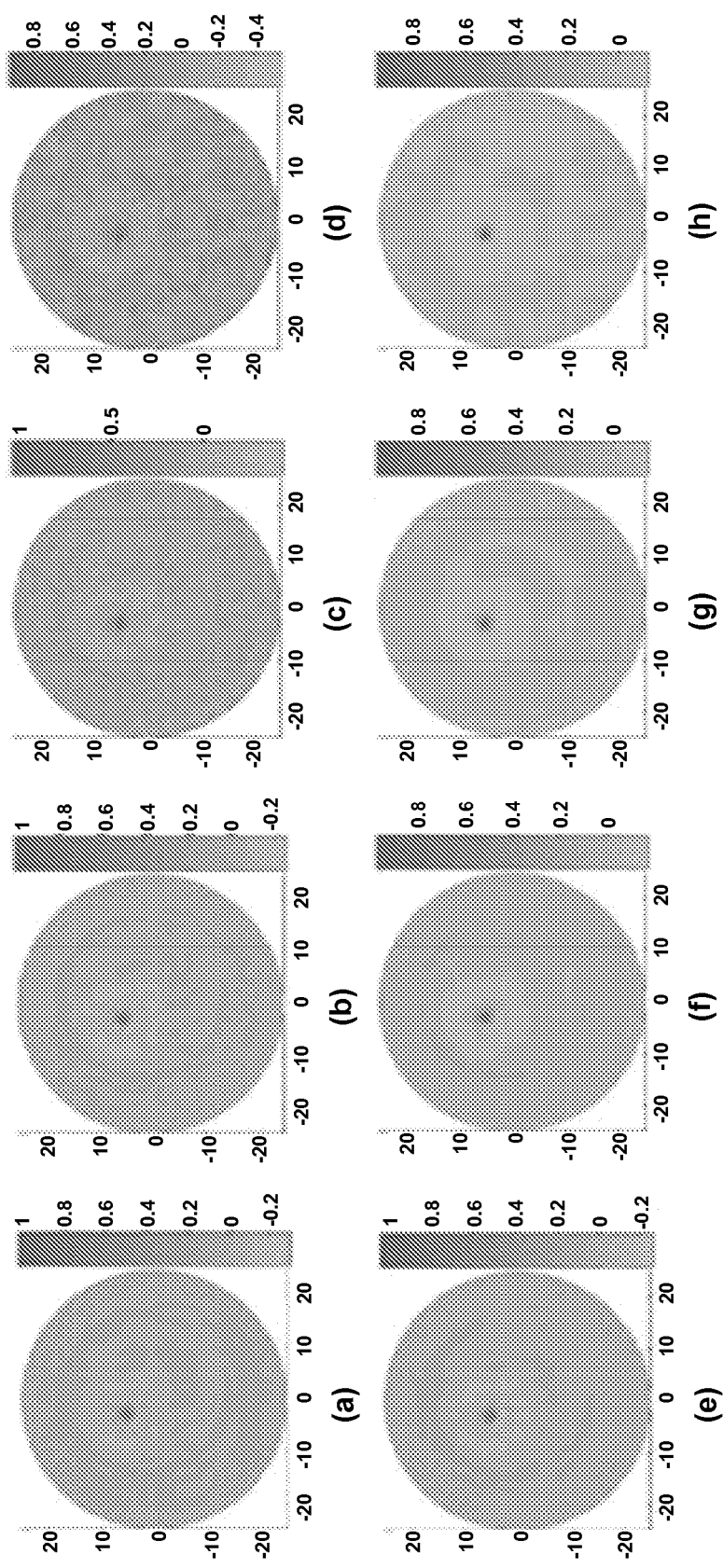

The reconstruction results based on data from the three experimental cases are shown in FIGS. 2, 3 and 4, respectively, using various numbers of detectors. In each figure, the images in the top and bottom rows, respectively, present the recovered absorbed energy density images using the algorithm without and with the TVM where 120, 60, 30, and 15 detectors were equally distributed along the surface of the circular background region.

FIG. 2 provides the reconstructed photoacoustic images based on data for the first case with two objects embedded in the phantom. FIG. 2(a) was reconstructed without TVM using data from 120 detectors, FIG. 2(b) was reconstructed without TVM using data from 60 detectors, FIG. 2(c) was reconstructed without TVM using data from 30 detectors, and FIG. 2(d) was reconstructed without TVM using data from 15 detectors. In comparison, FIG. 2(e) was reconstructed with TVM using data from 120 detectors, FIG. 2(f) was reconstructed with TVM using data from 60 detectors, FIG. 2(g) was reconstructed with TVM using data from 30 detectors, and FIG. 2(h) was reconstructed with TVM using data from 15 detectors. The conventional algorithm without the TVM provides high quality images only when the number of detectors was relatively sufficient as illustrated in FIGS. 2(a) and 2(b). As illustrated in FIGS. 2(c) and 2(d), the images reconstructed from data from fewer detectors by the conventional algorithm without the TVM contain severe artifacts and distortions. As can be seen in FIGS. 2(e)-2(h), the images do not exhibit the same degradation. Considerably enhanced images are achieved using the method with the TVM, especially when the number of the detectors is reduced to 30 or 15 as illustrated in FIGS. 2(g) and 2(h).

FIG. 3 provides the reconstructed photoacoustic images based on data for the second case with one object embedded in the phantom. FIG. 3(a) was reconstructed without TVM using data from 120 detectors, FIG. 3(b) was reconstructed without TVM using data from 60 detectors, FIG. 3(c) was reconstructed without TVM using data from 30 detectors, and FIG. 3(d) was reconstructed without TVM using data from 15 detectors. In comparison, FIG. 3(e) was reconstructed with TVM using data from 120 detectors, FIG. 3(f) was reconstructed with TVM using data from 60 detectors, FIG. 3(g) was reconstructed with TVM using data from 30 detectors, and FIG. 3(h) was reconstructed with TVM using data from 15 detectors. The embedded object is observable in FIGS. 3(a) and 3(b) where the conventional algorithm without the TVM provides high quality images when the number of detectors was relatively sufficient. However, the severe artifacts and distortions of FIGS. 3(c) and 3(d) make the object very difficult to detect. As can be seen in FIGS. 3(e)-3(h), the images do not exhibit the same degradation using the method with the TVM, especially when the number of the detectors is reduced as illustrated in FIGS. 3(g) and 3(h).

FIG. 4 provides the reconstructed photoacoustic images based on data for the third (or last) case with one object embedded in the phantom. FIG. 4(a) was reconstructed without TVM using data from 120 detectors, FIG. 4(b) was reconstructed without TVM using data from 60 detectors, FIG. 4(c) was reconstructed without TVM using data from 30 detectors, and FIG. 4(d) was reconstructed without TVM using data from 15 detectors. In comparison, FIG. 4(e) was reconstructed with TVM using data from 120 detectors, FIG. 4(f) was reconstructed with TVM using data from 60 detectors, FIG. 4(g) was reconstructed with TVM using data from 30 detectors, and FIG. 4(h) was reconstructed with TVM using data from 15 detectors. As expected, the conventional algorithm without the TVM provides high quality images only when the number of detectors was relatively sufficient, as in FIGS. 4(a) and 4(b), with increasingly severe artifacts and distortions, as in FIGS. 4(c) and 4(d), as the number of detectors is decreased. As shown in FIGS. 4(e)-4(h), considerably enhanced images are achieved using the method with the TVM, especially when the number of the detectors is reduced to 30 or 15. It was also noted that the computational efficiency of the TVM based algorithm for recovering a small absorber (FIG. 3) and a larger absorber (FIG. 4) is similar when the number of the detectors is insufficient.

Figure 5:
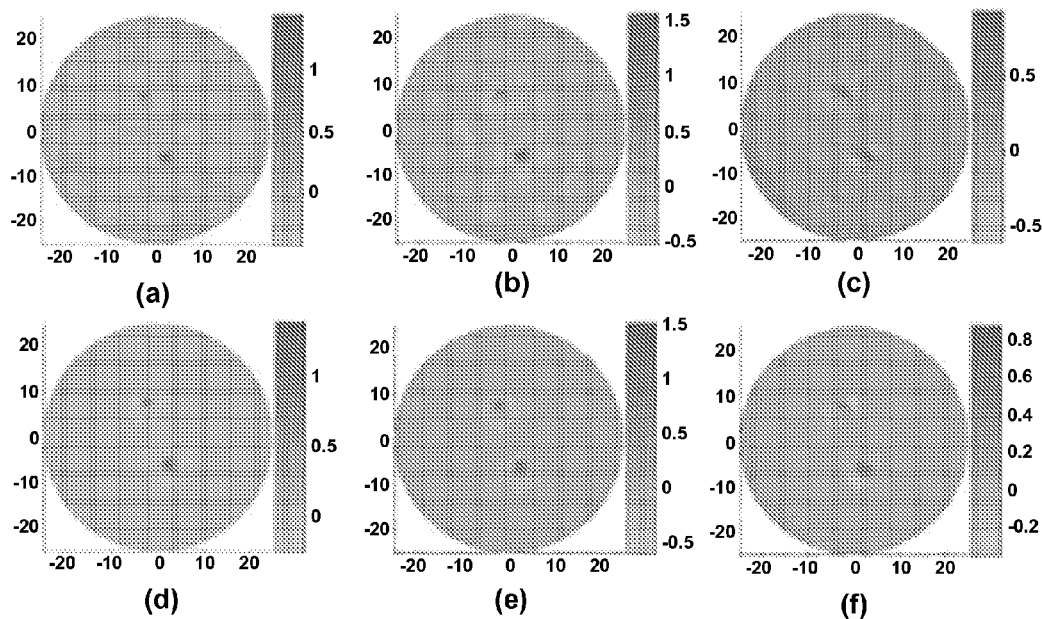

Images reconstructed from the limited-angle data for the first case using the two methods were also examined. The results are illustrated in FIG. 5 where the top and bottom rows show the recovered absorbed energy density images using the algorithm without and with TVM, respectively. FIG. 5(a) was reconstructed without TVM using data from 120 detectors equally distributed along the surface of the circular background region over 360°, FIG. 5(b) was reconstructed without TVM using data from 60 detectors equally distributed over 180°, and FIG. 5(c) was reconstructed without TVM using data from 30 detectors equally distributed over 90°. In contrast, FIG. 5(d) was reconstructed with TVM using data from 120 detectors equally distributed over 360°, FIG. 5(e) was reconstructed with TVM using data from 60 detectors equally distributed over 180°, and FIG. 5(f) was reconstructed with TVM using data from 30 detectors equally distributed over 90°. Again, strong artifacts and distortions exist in the images recovered with the method without the TVM when the data collected is angle-limited as illustrated in FIGS. 5(b) and 5(c), while considerably improved images are reconstructed using the TVM enhanced algorithm as shown in FIGS. 5(e) and 5(f).

In order to evaluate quantitatively the reconstruction quality using the method with and without TVM enhancement, the following universal quality index (UQI) was used:

$$UQI\{f^1 \cdot f^0\} = \frac{2Cov\{f^1 \cdot f^0\}}{(\sigma^1)^2 + (\sigma^0)^2} \frac{2\overline{f}^1 \overline{f}^0}{(\overline{f}^1)^2 + (\overline{f}^0)^2}. \qquad \text{EQN. (16)}$$

Here the image f can be interpreted as vectors of size N: $f=(f_1, f_2, \ldots f_N)^T$, where N denotes the number of image data acquired from the FEM based algorithm, $\overline{f}$ is the image means, $\sigma^j$ are the variances, and $Cov\{f^1, f^0\}$ is the covariances over the whole image domain, where j=0 and 1. UQI measures the image similarity between the reconstructed ($f^1$) and reference ($f^0$) images, and its value ranges between 0 and 1. The value of the UQI is closer to 1 when the reconstructed image is more similar to the reference image.

Figure 6:
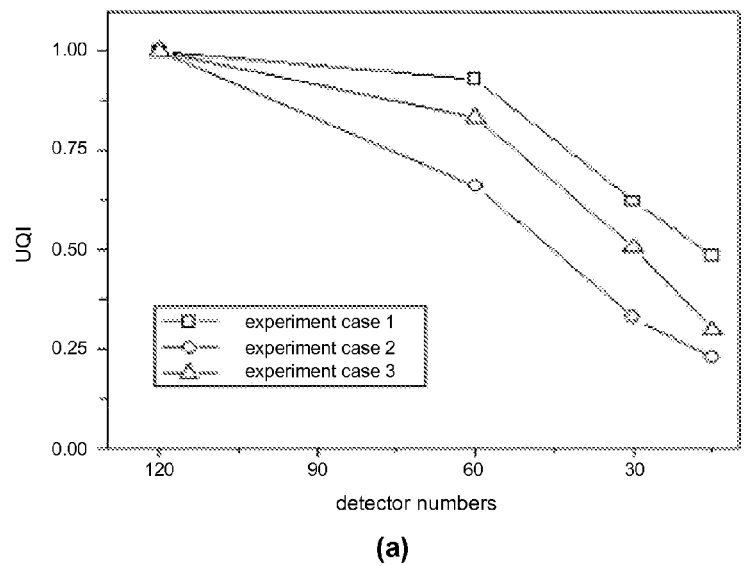
FIG. 6A-6C are plots of universal quality index (UQI) for the examples of FIGS. 2-5 in accordance with various embodiments of the present disclosure.
Figure 6:
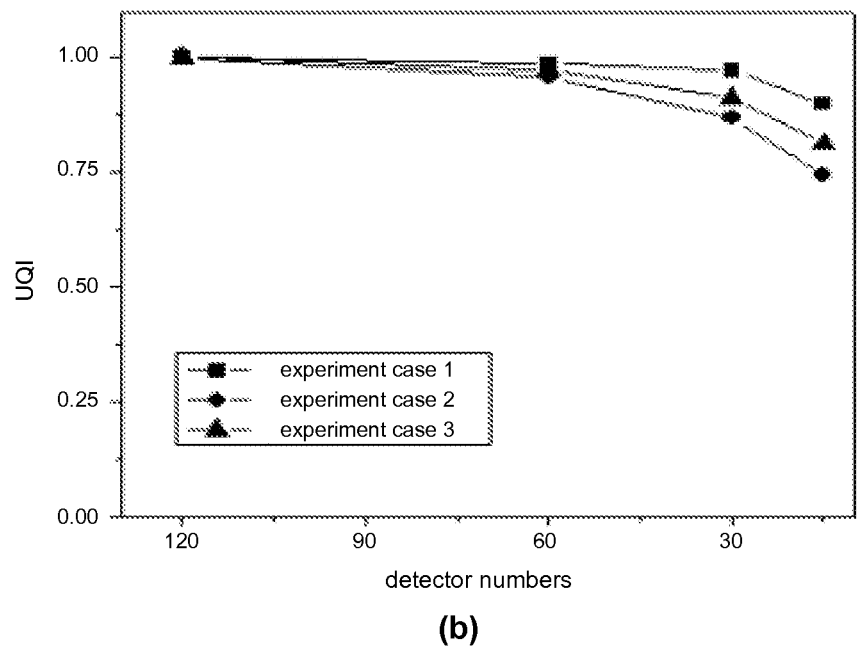
Figure 6:
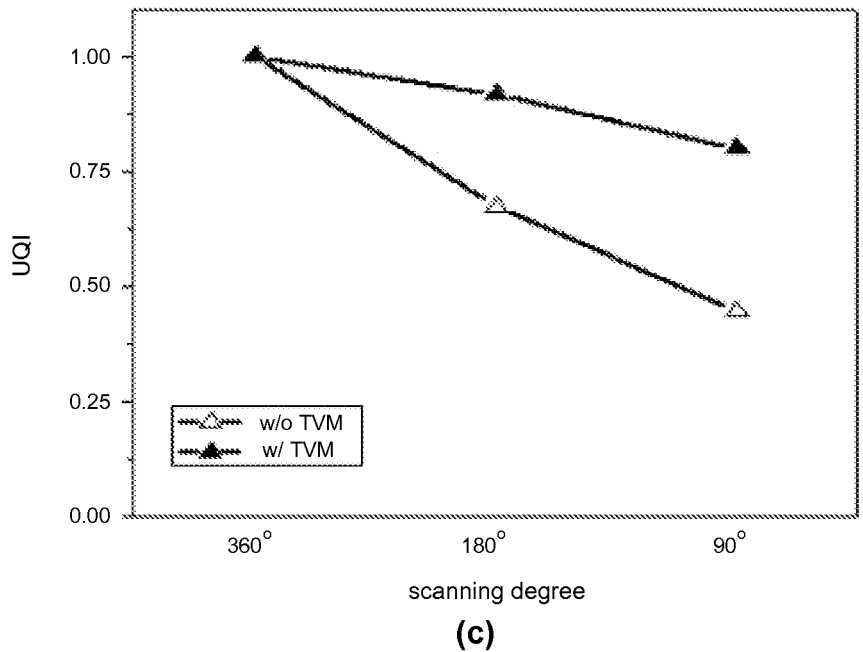

The UQIs was calculated for the three cases presented above, and the results are given in FIGS. 6A-6C where FIGS. 6A and 6B show the results from the data based on the method without and with the TVM, respectively, while FIG. 6C presents the results from the limited-angle data for the first case based on the two methods. Here the image data recovered by 120 detectors was regarded as the reference one. The computed UQIs shown in FIGS. 6A-6C confirm the observation that the TVM enhanced PAT algorithm provides significantly better image quality compared to the conventional method without the TVM.

Simulations were also carried out to evaluate the TVM method. In these simulations, a dual-meshing method was used for fast yet accurate inverse computation. The fine mesh used for the forward calculation consisted of 3627 nodes and 7072 elements, while the coarse mesh used for the inverse calculation had 930 nodes and 1768 elements. All the images obtained from the method without the TVM are the results of three iterations, while those obtained from the TVM-enhanced method are the results of 15 or more iterations. Parallel code was used to perform these calculations on Beowulf clusters with 8 central processing units (CPUs). The computational time may be further reduced if clusters with more than 8 CPUs are used. As mentioned earlier, the parameters $\omega_\Phi$ and $\delta$ were determined through numerical experimentation. A constant value of $\delta=0.001$ was sufficient for the current simulation and experimental studies, while the value of $\omega_\Phi$ was related to the signal-to-noise ratio of the measurements. For the simulations presented, $\omega_\Phi=0.5$ was used for cases 1, 2, and 3, and $\omega_\Phi=1.0$ was used for case 4.

Figure 7:
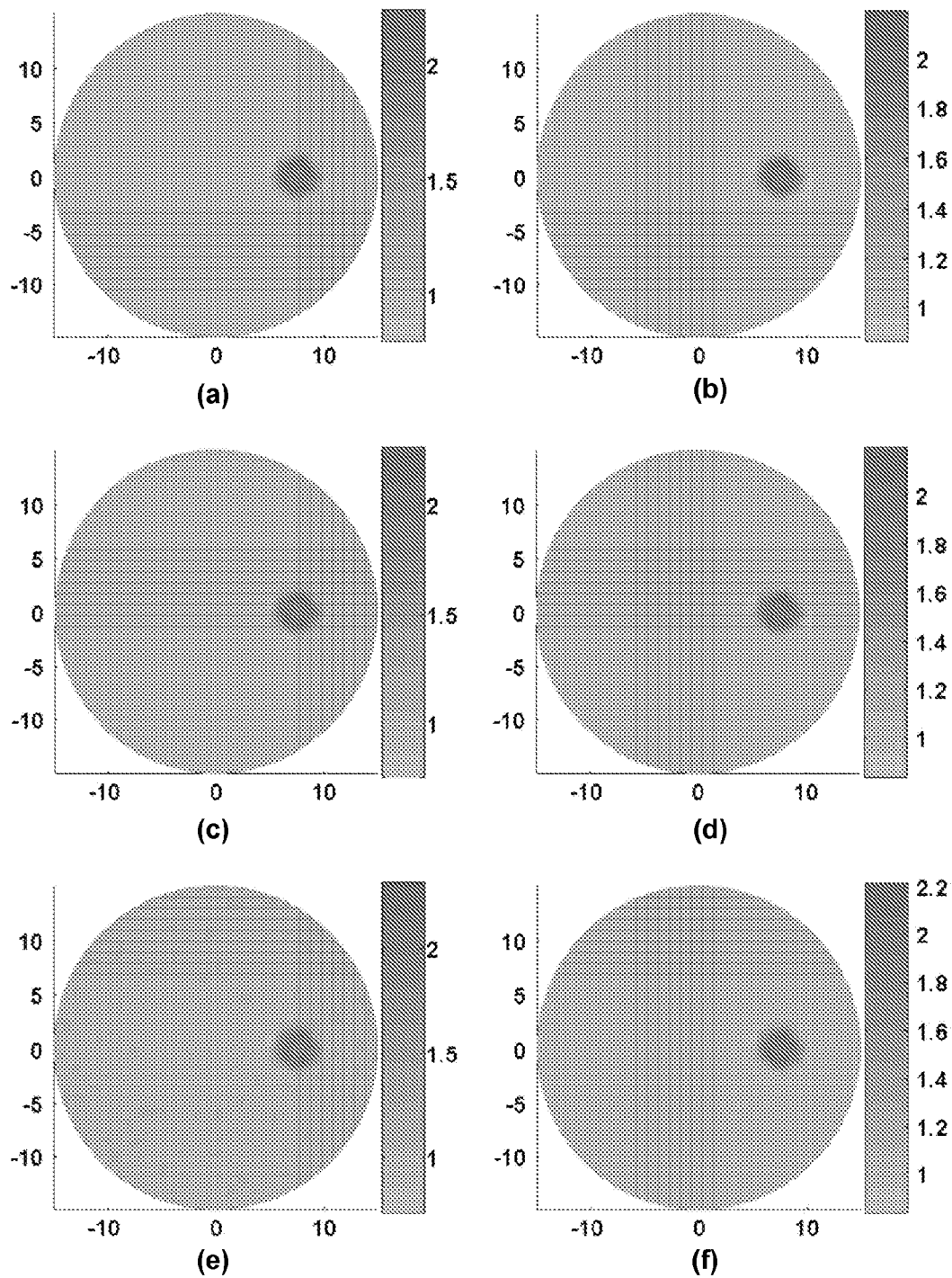
FIG. 7 provides examples of absorbed energy density images recovered using the reconstruction method without and with the TVM enhancement of FIGS. 1A and 1B under the conditions of different noise levels in accordance with various embodiments of the present disclosure.

For the first simulation, the test geometry is a 30 mm diameter circular background containing an off-center 4 mm diameter target region. The target had $\Phi=2.0$ mJ/mm$^3$, while the background had Φ=1.0 mJ/mm³. In this case, the image reconstruction was performed with 0%, 10%, and 25% noise added to the "measured" data. Referring to FIG. 7, shown are two sets of absorbed energy density images recovered using the reconstruction method without and with the TVM enhancement under the conditions of different noise levels. FIG. 7(a) is without the TVM and 0% noise, FIG. 7(b) is with the TVM and 0% noise, FIG. 7(c) is without the TVM and 10% noise, FIG. 7(d) is with the TVM and 10% noise, FIG. 7(e) is without the TVM and 25% noise, and FIG. 7(f) is with the TVM and 25% noise. The axes illustrate the spatial scale in millimeters, whereas the color (or shading) scale indicates the absorbed energy density in millijoules per cubic millimeter.

Figure 8:
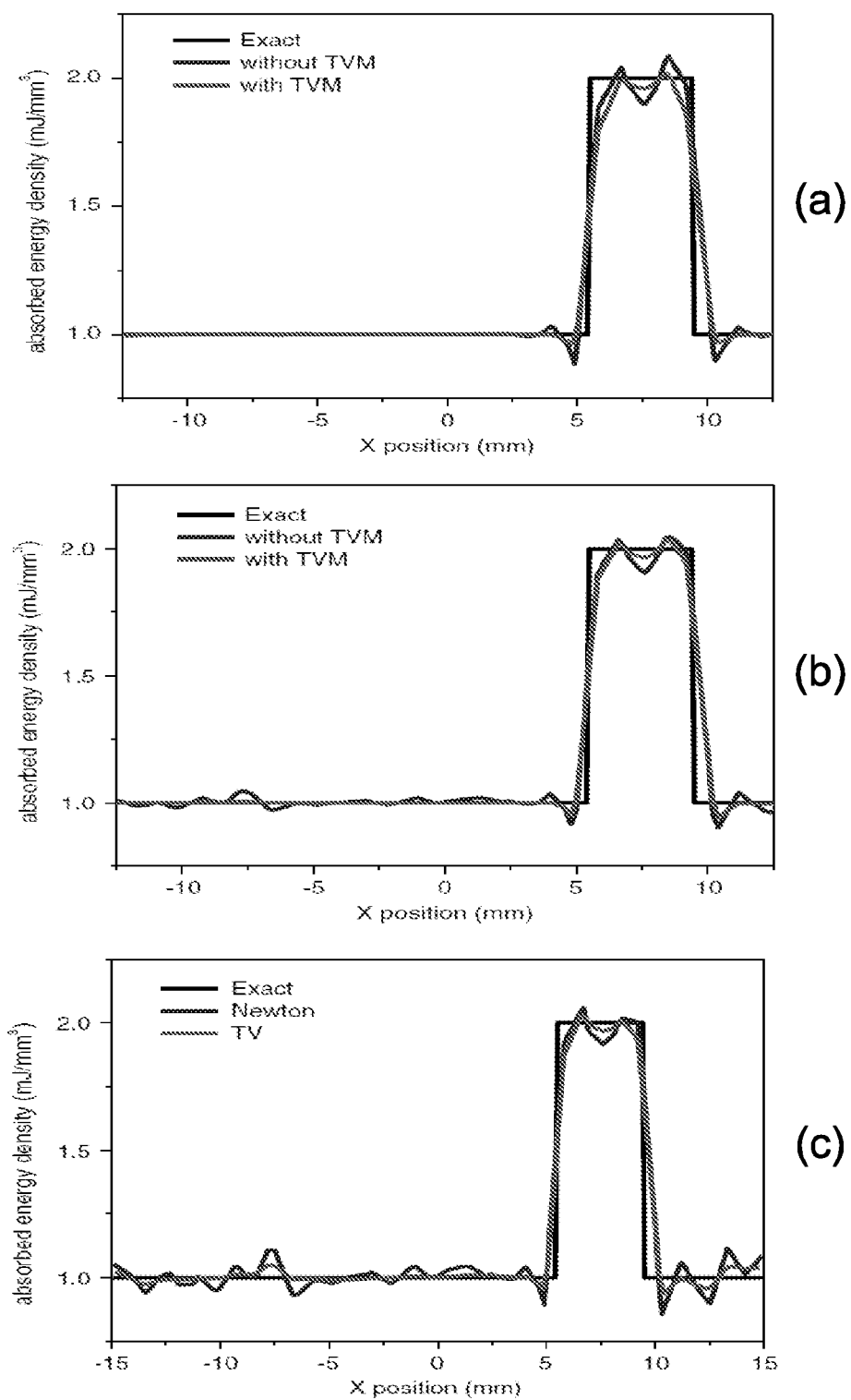
FIG. 8 includes the reconstructed absorbed energy density profiles along transects through the target for the images of FIG. 7 in accordance with various embodiments of the present disclosure.

As can be seen from FIG. 7, enhancement of the reconstruction by the incorporation of the TVM provides an improvement over the method without the TVM. To provide a more quantitative assessment of these images, FIG. 8 is included, in which the reconstructed absorbed energy density profiles are displayed along transects through the target for the images shown in FIG. 7. FIG. 8 provides a comparison of the exact and reconstructed absorbed energy density profiles along transect y=0 mm for the images (a) 0% noise, (b) 10% noise, and (c) 25% noise. The TVM-enhanced method not only can improve the quality of the recovered images, but also can decrease the sensitivity of the method to noise effect.

Figure 9:
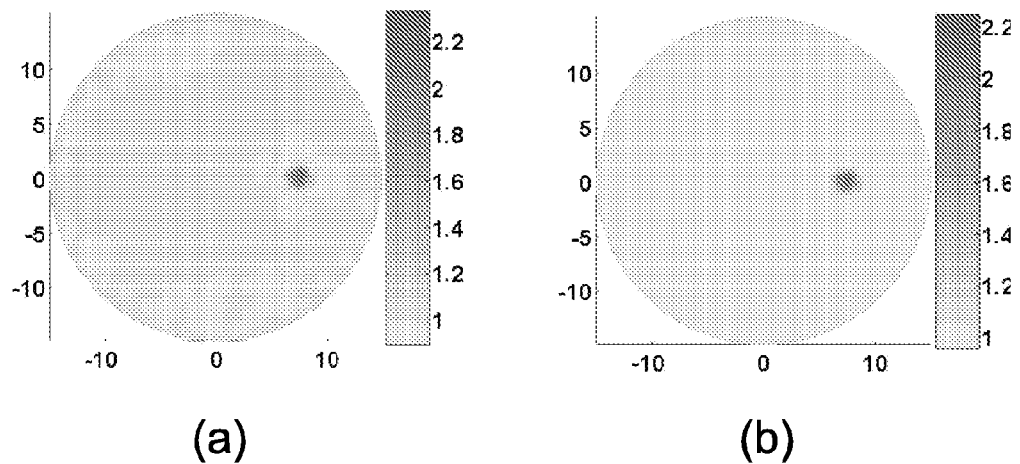
FIGS. 9-11 illustrate absorbed energy density images and the quantitative profiles of the absorbed energy density along transects through the target for the images in accordance with various embodiments of the present disclosure.
Figure 9:
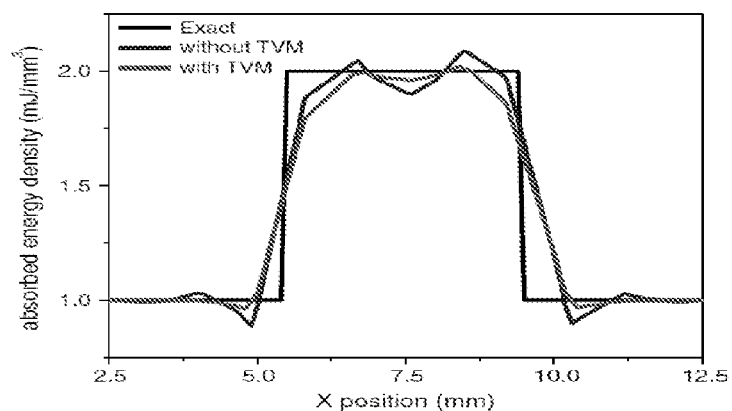
Figure 9:
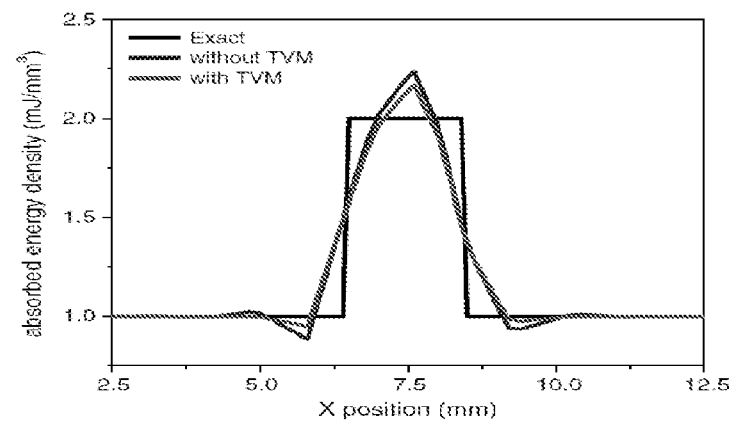

The second simulation was intended to investigate how the target size affects the TVM enhancement. In this case, no noise was added to the "measured" data, and the diameter of the off-center target was 2 mm. FIGS. 9(a) and 9(b) illustrate two sets of absorbed energy density images recovered using the method without the TVM and with the TVM enhancement, respectively. FIGS. 9(c) and 9(d) present the quantitative profiles of the absorbed energy density along transects (y=0 mm) through the target for the images shown in FIGS. 7(a)-7(b) and 9(a)-9(b), respectively. Again, considerable improvement can be observed from the reconstructed results when the TVM is invoked compared with the method without the TVM. It is also interesting to note that the enhancement for this case is more striking than that for the first one where the background contained a larger target.

Figure 10:
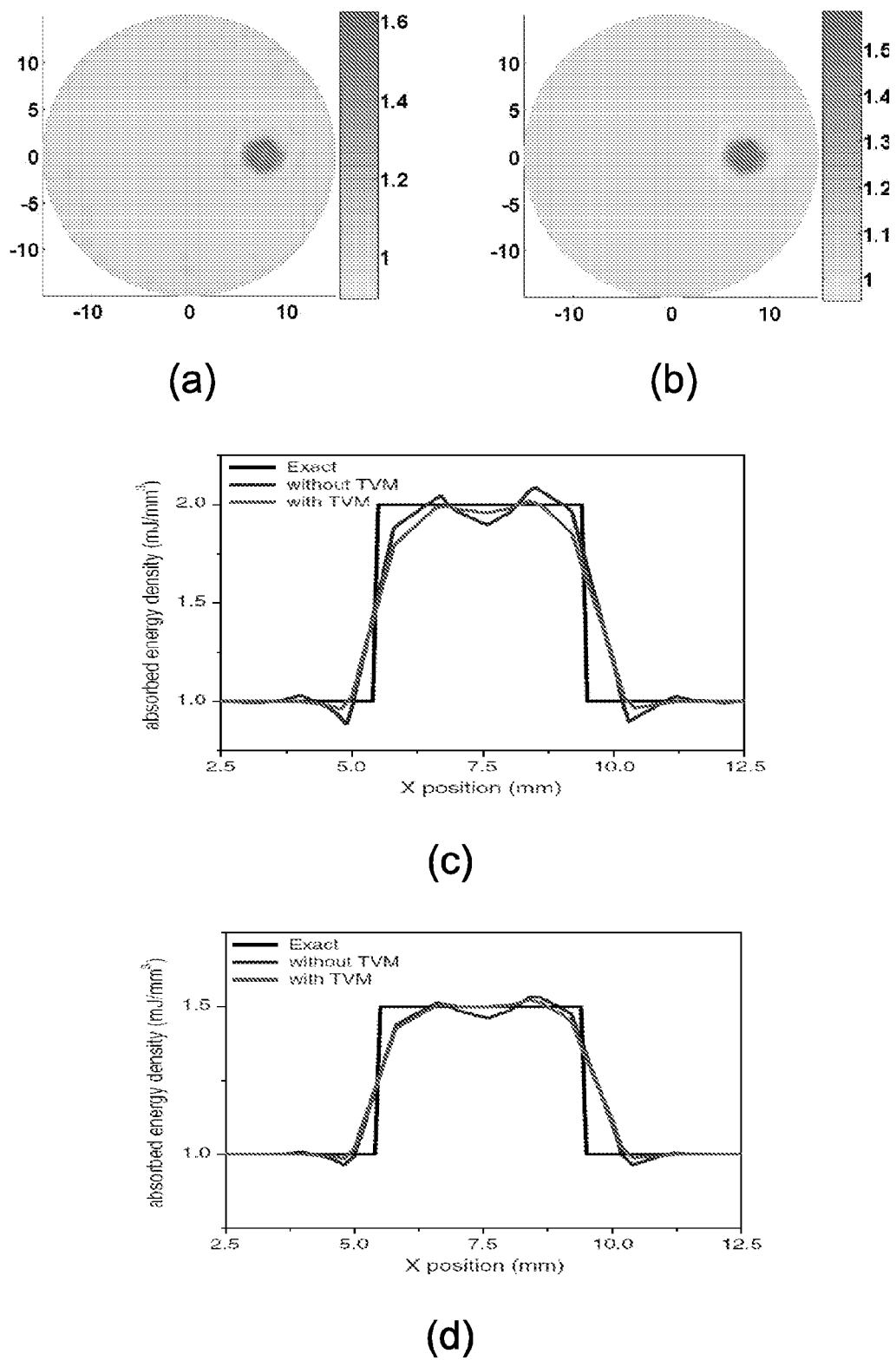

The third simulation aims to see how the contrast level of the absorbed energy density between the target and the background impacts the TVM enhancement. In this case, no noise was added to the "measured" data, and the off-center target had a diameter of 4 mm and Φ=1.5 mJ/mm³. FIGS. 10(a) and 10(b) present two sets of absorbed energy density images recovered using the method without the TVM and with the TVM enhancement, respectively. FIGS. 10(c) and 10(d) show the quantitative profiles of the absorbed energy density along transects (y=0 mm) through the target for the images shown in FIGS. 7(a)-7(b) and 10(a)-10(b), respectively. It can be seen that the images formed by incorporation of the TVM are clearly enhanced qualitatively in visual content relative to that obtained using the method without the TVM. Also note that lower the contrast level is, the larger the enhancement.

Figure 11:
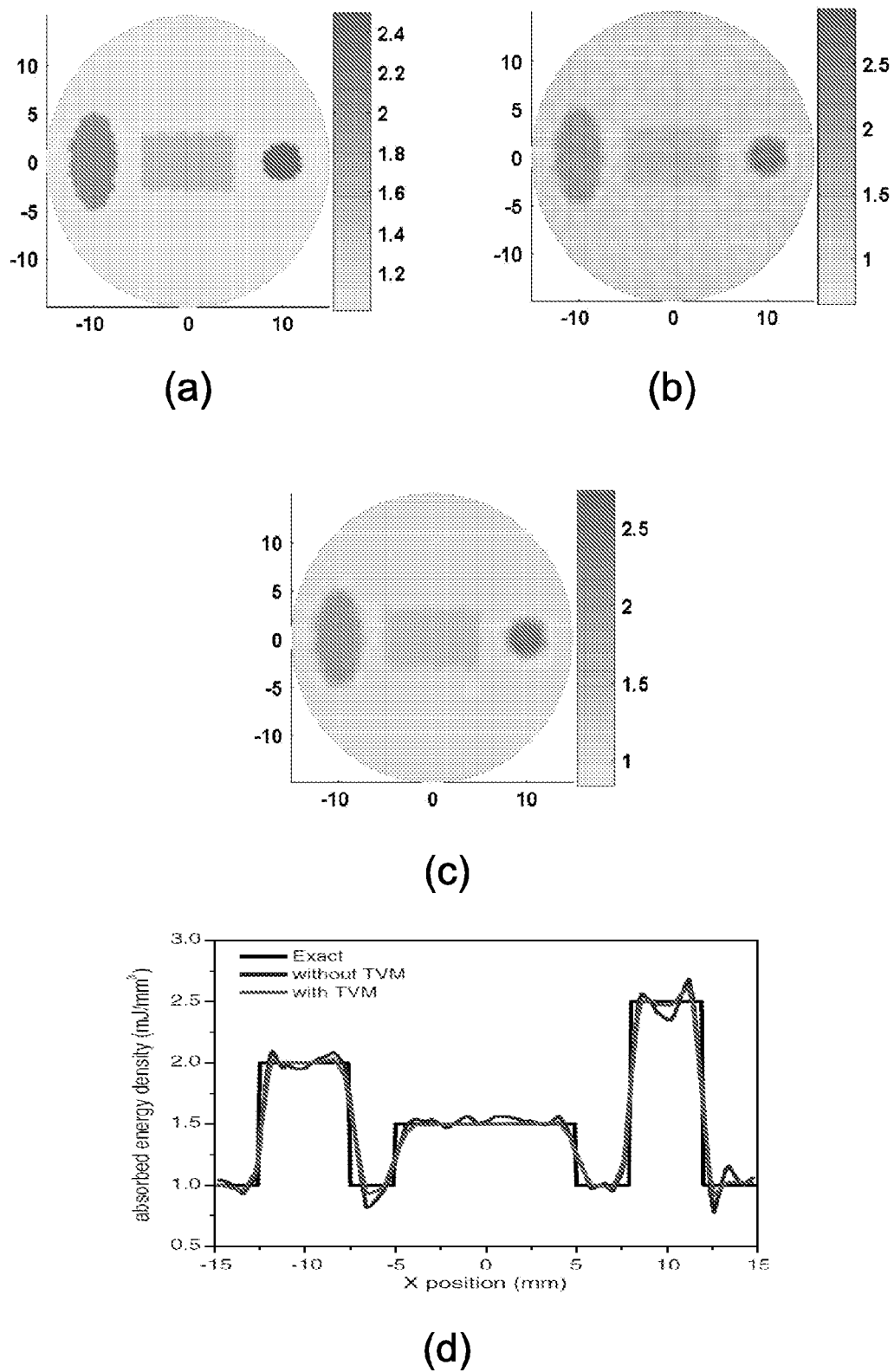

In the fourth simulation, three targets having different shapes (circular, elliptical, and rectangular) were embedded in the background, and the absorbed energy density of these targets was 2.5, 1.5, and 2.0 mJ/mm³, respectively. A noise level of 25% was added to the "measured" data in this case. FIG. 11 shows the exact and the recovered absorbed energy density images as well as the quantitative absorbed energy density property profiles along the transect that across these targets. FIG. 11(a) is the exact image, FIG. 11(b) is without the TVM, FIG. 11(c) is with the TVM, and FIG. 11(d) shows the absorbed energy density profiles along the transect y=0 mm. Again, an improvement in image quality is apparent.

Figure 12:
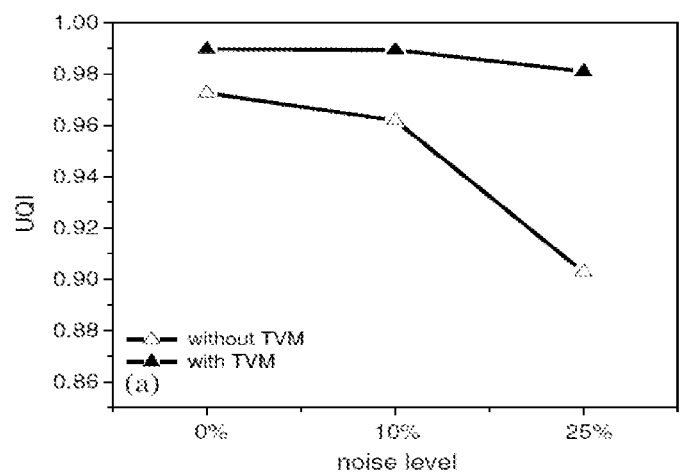
FIG. 12 provides the calculated UQIs for the simulation cases of FIGS. 7-11 in accordance with various embodiments of the present disclosure.
Figure 12:
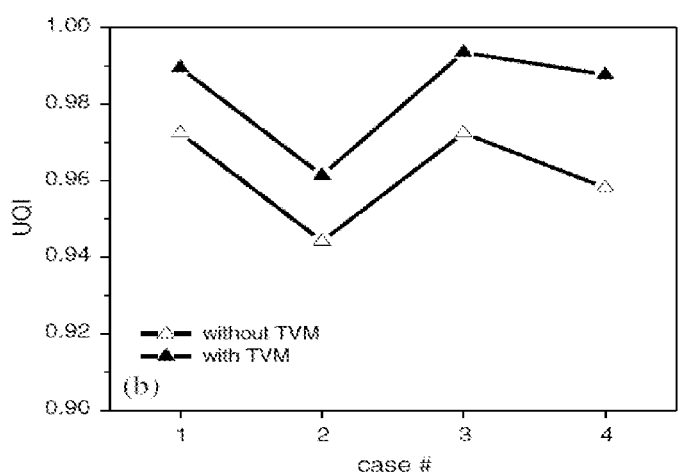

In order to quantitatively evaluate the reconstruction quality using the reconstruction method with and without TVM enhancement, we used the universal quality index (UQI) of EQN. 16 to measure the degree of similarity between the reconstructed and exact images. Referring to FIG. 12, shown are the calculated UQIs for the simulation cases. FIG. 12(a) depicts the UQIs for case 1 at the different noise levels and FIG. 12(b) depicts the UQIs for cases 2-4. As can be seen from FIG. 12, the TVM-based method provides significantly better UQIs than that without TVM.

Both phantom and in vivo experimental data were used to confirm our findings from the simulations. The experimental setup used for collecting the phantom data was a pulsed Nd:YAG laser based single transducer (1 MHz) scanning system. Three phantom experiments were conducted. In the first two experiments, one or two objects were embedded with a size ranging from 3 to 0.5 mm in a 50 mm diameter solid cylindrical phantom. The phantom materials used consisted of Intralipid as a scatterer and India ink as an absorber with Agar powder (1%-2%) for solidifying the Intralipid and India ink solution. The absorption coefficient of the background phantom was 0.01 mm⁻¹, while the absorption coefficient of the target(s) was 0.03 mm⁻¹. In the last experiment, a single target-containing phantom was used, aiming to test the capability of detecting targets having low optical contrasts relative to the background phantom. In this case, the target had an absorption coefficient of 0.015 mm⁻¹. The reduced scattering coefficients of the background phantom and targets were 1.0 and 3.0 mm⁻¹ for the first two experiments, and 1.0 and 2.0 mm⁻¹ for the last experiment.

A total of 120 receivers were equally distributed along the surface of the circular background region. In the reconstructions, the fine mesh used for the forward calculation consisted of 5977 nodes and 11,712 elements, while the coarse mesh used for the inverse calculation had 1525 nodes and 2928 elements. The reconstructed images were the results of three and 15 iterations for the method without and with the TVM, respectively. For these experimental cases, $\omega_\Phi$=1.0 and δ=0.001 were used for the cases 1 and 3 and $\omega_\Phi$=2.0 and δ=0.001 were used for case 2.

It should be noted that, in the experimental situation, the effect of ultrasonic transducer response should be considered in the PAT image reconstruction because the transducer mechanical-electrical impulse response as well as the transducer aperture effect may introduce significant errors in the forward model. To reduce these effects in the calculations, the normalized acoustic pressure distribution was applied in the reconstruction and used the appropriate parameters (initial values, etc.) obtained from an optimization/searching method.

Figure 13:
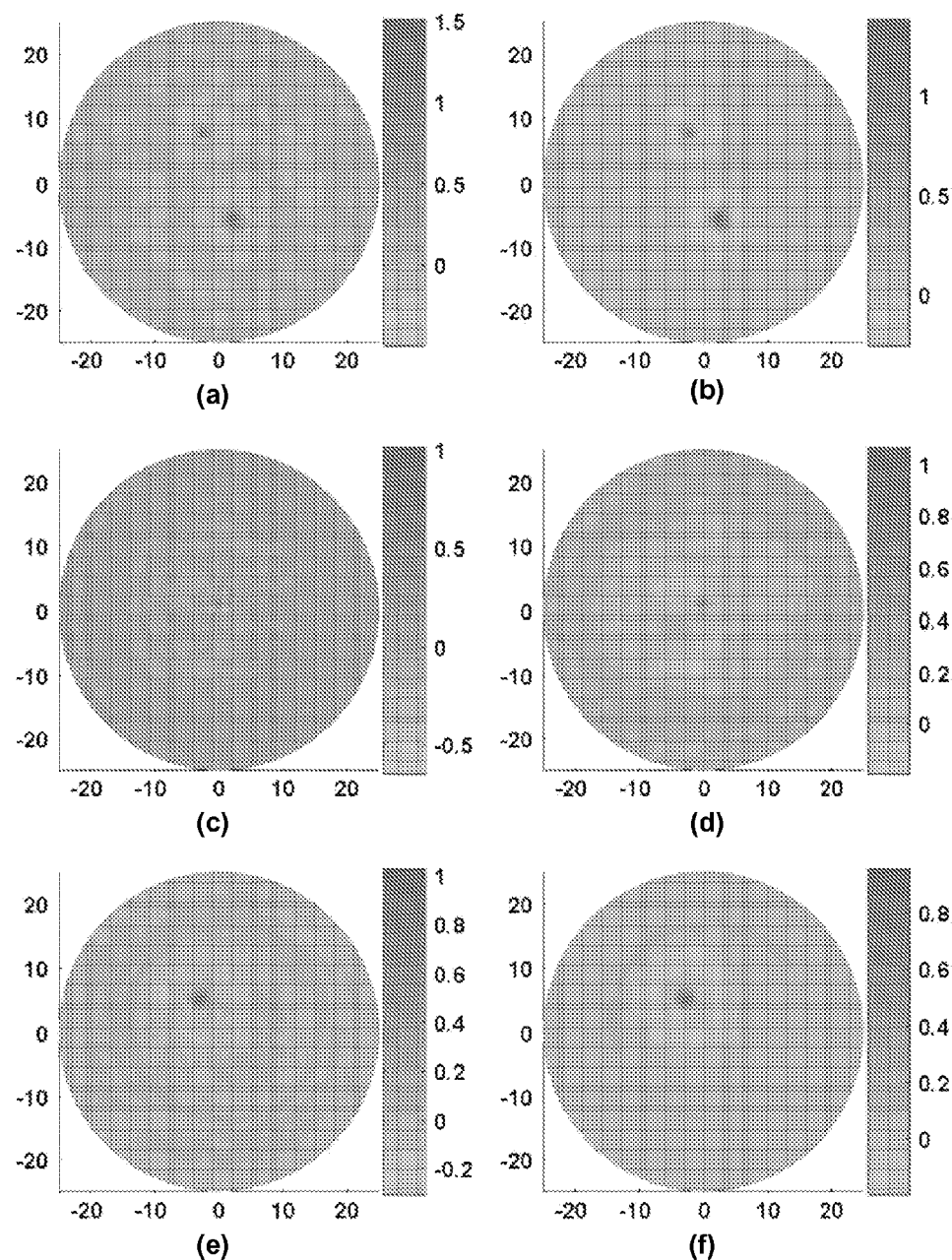
FIG. 13 illustrates the reconstructed absorbed energy density images for three experimental cases in accordance with various embodiments of the present disclosure.
Figure 14:
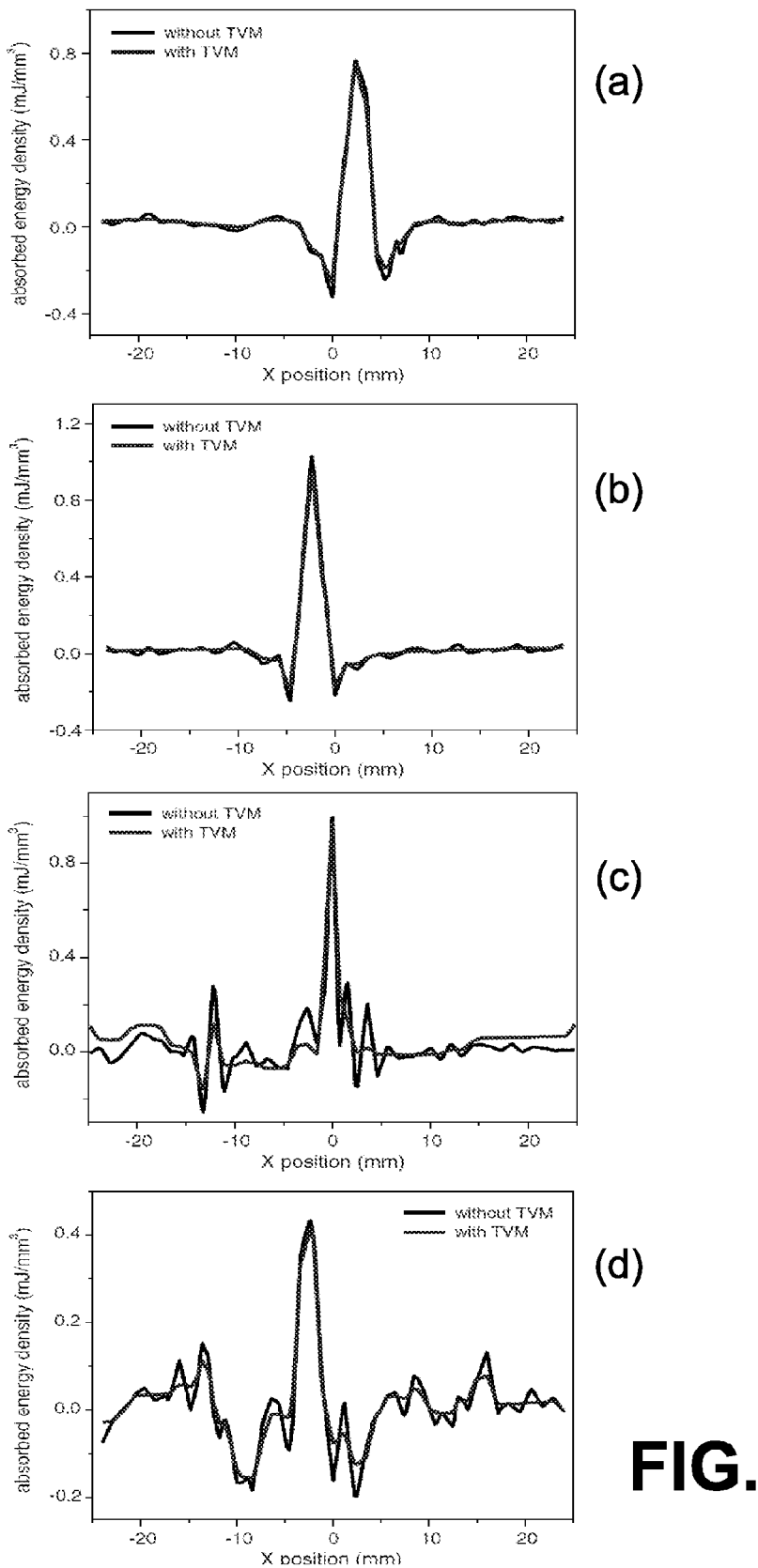
FIG. 14 provides quantitative absorption coefficient profiles along transects through one target for the images in FIG. 13 in accordance with various embodiments of the present disclosure.

Referring to FIG. 13, shown are the reconstructed absorbed energy density images for all the three experimental cases. FIG. 13(a) illustrates case 1 without the TVM, FIG. 13(b) illustrates case 1 with the TVM, FIG. 13(c) illustrates case 2 without the TVM, FIG. 13(d) illustrates case 2 with the TVM, FIG. 13(e) illustrates case 3 without the TVM, and FIG. 13(f) illustrates case 3 with the TVM. The axes illustrate the spatial scale in millimeters, whereas the shade (or color) scale records the absorbed energy density in millijoules per cubic millimeter. FIG. 14 presents quantitative absorption coefficient profiles along transects through one target for the images shown in FIG. 13. FIG. 14(a) is the recovered absorbed energy density profile along y=−7.0 mm crossing the 3 mm diameter target for experimental case 1, FIG. 14(b) is along y=8.0 mm crossing the 2 mm diameter target for experimental case 1, FIG. 14(c) is along y=1.0 mm for experimental case 2, and FIG. 14(d) is along y=6.5 mm for experimental case 3. Enhanced images are achieved with the TVM, especially when the target is small (case 2), or when the contrast level between the target and the background is low (case 3).

Figure 15:
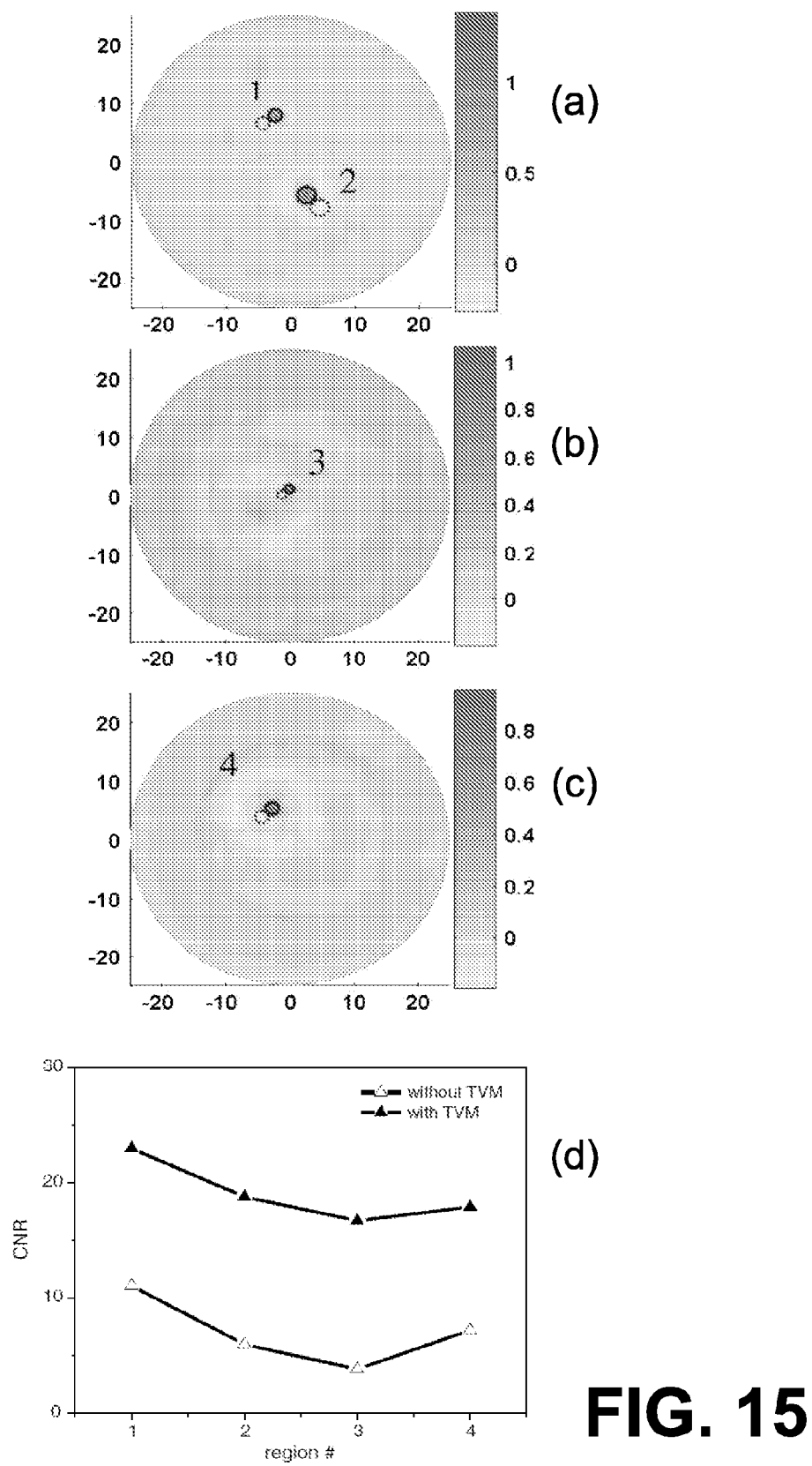
FIG. 15 illustrates the t-ROI and b-ROI and the contrast-to-noise ratio (CNR) for the three experimental cases in FIG. 13 in accordance with various embodiments of the present disclosure.

Because there is no true or exact image available for the experimental cases, we used the contrast-to-noise ratio (CNR) to quantitatively evaluate the experimental results. To compute CNR, two regions of interest (ROIs) were selected, each having the same size. One region is in the target (referred as t-ROI) and the other is in the background (denoted as b-ROI). The CNR is defined as $$CNR = \frac{|\bar{f}^{(t)} - \bar{f}^{(b)}|}{\sigma^{(b)}}.$$  EQN. (17)

where $\bar{f}^{(t)}$ and $\bar{f}^{(b)}$, respectively, denote the mean over the t-ROI and b-ROI, and $\sigma^{(b)}$ denotes the variances over the b-ROI. Referring to FIGS. 15(a), 15(b), and 15(c), solid and dashed circles are used to express the t-ROI and b-ROI for the three experimental cases. The CNR was calculated for each pair of the t- and b-ROIs using Eq. (17) and the results are presented in FIG. 15(d). It can be seen that the CNR obtained using the method with TVM is clearly larger than that using the method without TVM, indicating that the TVM based method is less sensitive to the noise effects.

As a final example, the TVM method was tested using in vivo data collected previously from an animal (rat) model of epilepsy. Focal seizures were induced by microinjection of bicuculline methiodide (BMI) into the parietal neocortex. The in vivo data were collected using the same pulsed Nd:YAG laser-based scanning PAT system. In the reconstruction, the fine mesh used for the forward calculation consisted of 17,713 nodes and 34,944 elements, while the coarse mesh used for the inverse calculation had 4489 nodes and 8736 elements. The in vivo images obtained were the results of two and five iterations for the methods without and with the TVM, respectively. It was found that $\omega_\Phi$=0.1 and $\delta$=0.001 appeared to provide optimal results.

Figure 16:
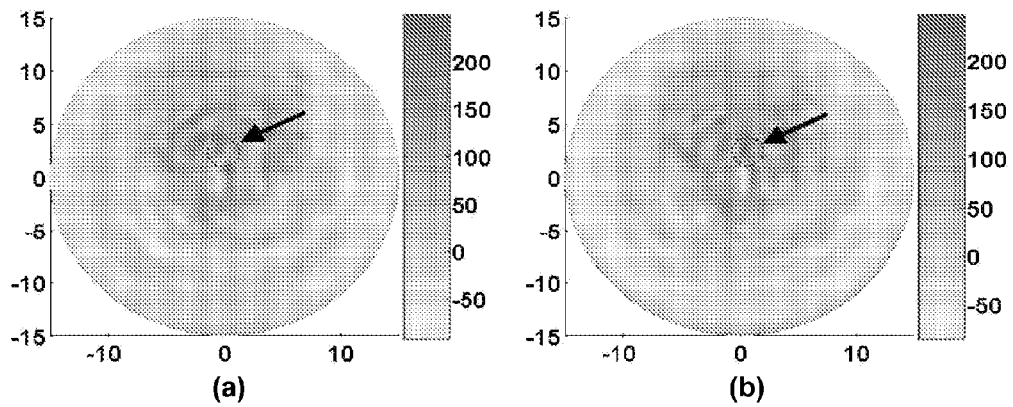
FIG. 16 illustrates the recovered images of an in vivo test in accordance with various embodiments of the present disclosure.

FIG. 16 illustrates the recovered images for the rat brain scanned 10 min after the injection of BMI without and with the use of the TVM. The in vivo results shown here confirm that both of the reconstruction methods can provide quality images (the arrow indicates the detected seizure focus), while notable enhancement in image quality can be observed with the TVM-based method. For example, the actual continuous middle cerebral artery (indicated by the dashed circle) is shown discontinued in FIG. 16(a) (without the TVM), while this feature is clearly depicted in FIG. 16(b) (with the TVM).

Figure 17:
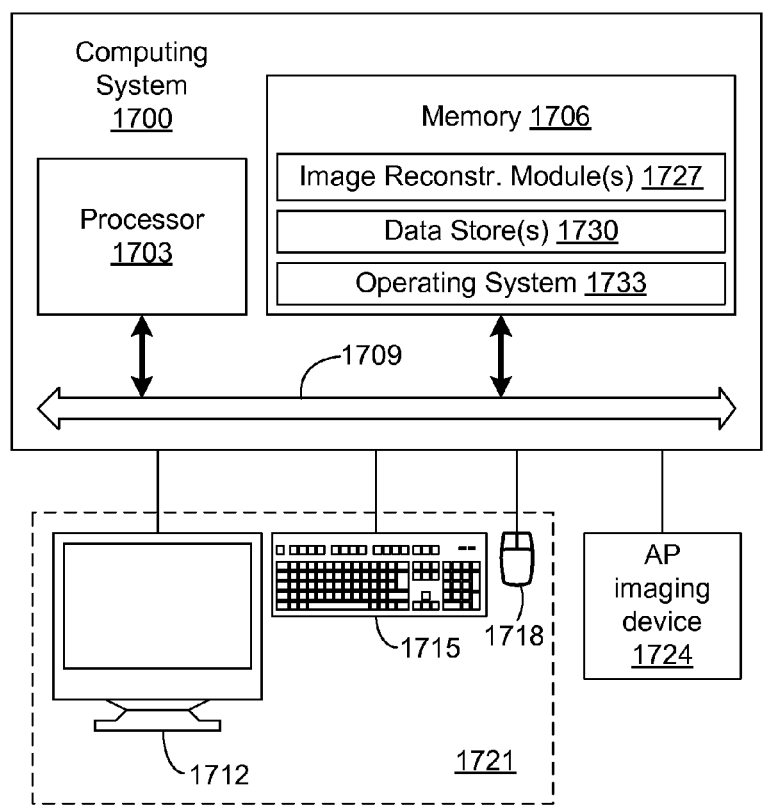
FIG. 17 is a schematic block diagram of a computing system in accordance with various embodiments of the present disclosure.

With reference to FIG. 17, shown is a schematic block diagram of a computing system 1700 in accordance with various embodiments of the present disclosure. The computing system 1700 includes at least one processor circuit, for example, having a processor 1703 and a memory 1706, both of which are coupled to a local interface 1709. To this end, the computing system 1700 may comprise, for example, at least one computer or like device. The local interface 1709 may comprise, for example, a data bus with an accompanying address/control bus or other bus structure as can be appreciated. In addition, the computing system 1700 includes operator interface devices such as, e.g., a display device 1712, a keyboard 1715, and/or a mouse 1718. In some implementations, the operator interface device may be interactive display 1721 (e.g., a touch screen) that provides various functionality for operator interaction with the computing system 1700. Various imaging systems such as, e.g., PA imaging device 1724 may also interface with the computing system 1700 to allow for acquisition of EEG signals from a subject. In some embodiments, the PA imaging device 1724 may be an array of detectors configured to be positioned about the monitored object or volume.

Stored in the memory 1706 are both data and several components that are executable by the processor 1703. In particular, stored in the memory 1706 and executable by the processor 1703 are various application modules or programs such as, e.g., an image reconstruction module, application, or program 1727 and/or other applications. Also stored in the memory 1706 may be a data store 1730 and other data. In addition, an operating system 1733 may be stored in the memory 1706 and executable by the processor 1703.

It is understood that there may be other applications that are stored in the memory 1706 and are executable by the processor 1703 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, or other programming languages.

A number of software components are stored in the memory 1706 and are executable by the processor 1703. In this respect, the term "executable" means a program file that is in a form that can ultimately be run by the processor 1703. Examples of executable programs may be, for example, a compiled program that can be translated into machine code in a format that can be loaded into a random access portion of the memory 1706 and run by the processor 1703, source code that may be expressed in proper format such as object code that is capable of being loaded into a random access portion of the memory 1706 and executed by the processor 1703, or source code that may be interpreted by another executable program to generate instructions in a random access portion of the memory 1706 to be executed by the processor 1703, etc. An executable program may be stored in any portion or component of the memory 1706 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 1706 is defined herein as including both volatile and nonvolatile memory and data storage components. Volatile components are those that do not retain data values upon loss of power. Nonvolatile components are those that retain data upon a loss of power. Thus, the memory 1706 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 1703 may represent multiple processors 1703 and the memory 1706 may represent multiple memories 1706 that operate in parallel processing circuits, respectively. In such a case, the local interface 1709 may be an appropriate network that facilitates communication between any two of the multiple processors 1703, between any processor 1703 and any of the memories 1706, or between any two of the memories 1706, etc. The processor 1703 may be of electrical or of some other available construction.

Although the image reconstruction module, application, or program 1727 and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Although the flowcharts of FIGS. 1A and 1B show a specific order of execution, it is understood that the order of execution may differ from that which is depicted. For example, the order of execution of two or more blocks may be scrambled relative to the order shown. Also, two or more blocks shown in succession in FIGS. 1A and 1B may be executed concurrently or with partial concurrence. Further, in some embodiments, one or more of the blocks shown in FIGS. 1A and 1B may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the image reconstruction module, application, or program 1727 and/or application(s), that comprises software or code can be embodied in any non-transitory computer-readable medium for use by or in connection with an instruction execution system such as, for example, a processor 1703 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, at least the following is claimed:

1. A method, comprising:
    obtaining photoacoustic data;
    reconstructing a reconstructed image from the photoacoustic data using total-variation minimization based photoacoustic tomography reconstruction, where the total-variation minimization based photoacoustic tomography reconstruction is based at least in part upon a functional including observed acoustic field data and computed acoustic field data and a penalty term based upon variation of absorbed energy density ($\Phi$); and
    providing the reconstructed image for rendering on a display device.

2. The method of claim 1, where in the penalty term is given by $$L(\Phi)=\int\sqrt{\omega_\Phi^2|\nabla\Phi|^2+\delta^2}\,dxdy.$$

3. The method of claim 1, wherein the total-variation minimization based photoacoustic tomography reconstruction is complete when the functional satisfies a predefined threshold.

4. The method of claim 1, wherein the total-variation minimization based photoacoustic tomography reconstruction is performed for a predefined number of iterations.

5. The method of claim 1, wherein the total-variation minimization based photoacoustic tomography reconstruction compensates for an effect of ultrasonic transducer response.

6. The method of claim 5, wherein a normalized acoustic pressure distribution is applied to compensate for the effect of ultrasonic transducer response.

7. The method of claim 1, wherein the reconstructed image is rendered with a color scale indicating the absorbed energy density.

8. The method of claim 1, wherein the photoacoustic data is photoacoustic time-domain data or photoacoustic frequency-domain data.

9. The method of claim 1, wherein the total-variation minimization based photoacoustic tomography reconstruction includes a dual-meshing scheme with forward calculation of a first mesh and inverse calculation of a second mesh.

10. The method of claim 9, wherein the second mesh is a course mesh including fewer nodes and elements than the first mesh.

11. A system, comprising:
    at least one computing device;
    an image reconstruction program executable in the at least one computing device, the image reconstruction program comprising:
        logic that obtains photoacoustic data;
        logic that reconstructs a reconstructed image from the photoacoustic data using total-variation minimization based photoacoustic tomography reconstruction, where the total-variation minimization based photoacoustic tomography reconstruction is based at least in part upon a functional including observed acoustic field data and computed acoustic field data and a penalty term based upon variation of absorbed energy density ($\Phi$); and logic that provides the reconstructed image for rendering on a display device.

12. The system of claim 11, where in the penalty term is given by $$L(\Phi) = \int \sqrt{\omega_\Phi^2 |\nabla \Phi|^2 + \delta^2}\, dx\, dy.$$

13. The system of claim 11, wherein the total-variation minimization based photoacoustic tomography reconstruction is complete when the functional satisfies a predefined threshold.

14. The system of claim 11, wherein the total-variation minimization based photoacoustic tomography reconstruction is performed for a predefined number of iterations.

15. The system of claim 11, wherein the total-variation minimization based photoacoustic tomography reconstruction compensates for an effect of ultrasonic transducer response.

16. The system of claim 15, wherein a normalized acoustic pressure distribution is applied to compensate for the effect of ultrasonic transducer response.

17. A system, comprising:
at least one computing device;
an image reconstruction program executable in the at least one computing device, the image reconstruction program comprising:
logic that obtains photoacoustic data;
logic that reconstructs a reconstructed image from the photoacoustic data using total-variation minimization based photoacoustic tomography reconstruction, where the total-variation minimization based photoacoustic tomography reconstruction includes a dual-meshing scheme with forward calculation of a first mesh and inverse calculation of a second mesh; and
logic that provides the reconstructed image for rendering on a display device.

18. The system of claim 17, wherein the second mesh is a course mesh including fewer nodes and elements than the first mesh.

19. The system of claim 11, wherein the photoacoustic data is obtained from memory.

20. The system of claim 11, wherein the photoacoustic data is photoacoustic time-domain data or photoacoustic frequency-domain data.

* * * * *